(12) United States Patent
Krumhar et al.

(10) Patent No.: US 6,528,502 B1
(45) Date of Patent: Mar. 4, 2003

(54) COMPOSITION AND METHOD FOR IMPROVED CARBOHYDRATE MANAGEMENT IN MAMMALS

(75) Inventors: Kim Carleton Krumhar, Carlsbad, CA (US); Jeffrey J. Katke, San Clemente, CA (US)

(73) Assignee: Metagenics, Inc., San Clemente, CA (US)

( * ) Notice: Subject to any disclaimer, the term of this patent is extended or adjusted under 35 U.S.C. 154(b) by 8 days.

(21) Appl. No.: 09/633,926

(22) Filed: Aug. 8, 2000

(51) Int. Cl.$^7$ .................. A61K 31/455; A61K 31/555; A61K 33/24; A61K 31/525; A61K 31/185; A61K 31/315

(52) U.S. Cl. ..................... 514/188; 514/23; 514/53; 514/54; 514/251; 514/276; 514/356; 514/494; 514/505; 514/553; 514/578; 514/781; 514/784; 514/866; 514/904; 514/905; 514/909; 514/910; 514/911; 424/646; 424/655; 426/72; 426/74; 426/810

(58) Field of Search .................. 514/23, 53, 54, 514/188, 251, 276, 356, 494, 505, 553, 578, 781, 784, 866, 904–905, 909–911; 424/646, 655; 426/72, 74, 810

(56) References Cited

U.S. PATENT DOCUMENTS

| 5,164,384 A | | 11/1992 | Paul ........................... 514/188 |
| 5,292,538 A | * | 3/1994 | Paul et al. ..................... 426/74 |
| 5,422,125 A | | 6/1995 | Skyler et al. ................. 424/646 |
| 5,443,838 A | | 8/1995 | Koenig, Jr. ................... 424/39 |
| 5,536,509 A | * | 7/1996 | Protti ............................. 426/2 |
| 5,543,405 A | | 8/1996 | Keown et al. ............... 514/188 |
| 5,550,113 A | | 8/1996 | Mann ........................... 514/54 |
| 5,569,458 A | * | 10/1996 | Greenberg .................. 424/726 |
| 5,614,224 A | | 3/1997 | Womack ...................... 424/646 |
| 5,639,471 A | | 6/1997 | Chait et al. .................. 424/439 |
| 5,730,988 A | | 3/1998 | Womack ...................... 424/774 |
| 5,770,215 A | * | 6/1998 | Moshyedi .................... 424/440 |
| 5,846,569 A | * | 12/1998 | Anderson et al. ........... 424/535 |
| 5,962,030 A | | 10/1999 | Fine ............................ 424/646 |
| 5,976,548 A | * | 11/1999 | Hsia et al. ................... 424/735 |
| 5,977,059 A | | 11/1999 | Khoo et al. .................... 514/2 |
| 5,994,295 A | | 11/1999 | Khoo et al. .................... 514/2 |
| 6,039,978 A | | 3/2000 | Bangs et al. ................. 424/489 |
| 6,039,989 A | | 3/2000 | Bangs et al. ................. 426/106 |
| 6,102,706 A | | 8/2000 | Khoo et al. .................. 434/127 |
| 6,132,724 A | | 10/2000 | Blum ........................... 424/725 |
| 6,291,533 B1 | * | 9/2001 | Fleischner ................... 514/682 |
| 6,447,809 B1 | * | 9/2002 | Krumhar et al. ............. 424/602 |
| 6,451,341 B1 | * | 9/2002 | Slaga et al. .................. 424/468 |

* cited by examiner

Primary Examiner—John Pak
(74) Attorney, Agent, or Firm—Knobbe, Martens, Olson & Bear LLP

(57) ABSTRACT

A nutritional supplement for use in managing carbohydrates and enhancing anabolism in mammals is described. The nutritional supplement contains regulated amounts of niacin, chromium, and vanadium, and optionally thiamin, riboflavin, magnesium, and zinc. These vitamins and minerals mimic and/or enhance the physiological effects of insulin in the body. A method of using the composition is also described.

1 Claim, No Drawings

COMPOSITION AND METHOD FOR IMPROVED CARBOHYDRATE MANAGEMENT IN MAMMALS

BACKGROUND OF THE INVENTION

This invention relates to dietary supplement. More particularly, the invention relates to a nutritional supplement and methods of use thereof for improved carbohydrate management in mammals.

As is well known in the medical community, insulin is one of the most powerful anabolic hormones in the body and is the primary driver of amino acid and glucose into muscle cells. In muscle tissue, insulin initiates the transport of glucose, mineral ions, and amino acids, and also regulates the synthesis and degradation of macromolecules. Additionally, insulin decreases muscle catabolism during exercise, which allows greater gains from intense exercise. It has been found that increased insulin activity affects tissues, and in particular muscle tissue, in a manner such that increased protein synthesis and muscle growth can occur.

Although insulin is primarily known for its ability to promote tissue uptake of blood sugar, i.e., glucose, it exerts a number of other important physiological effects. These effects include increased synthesis and retention of protein in skeletal muscle and other tissues; stimulation of activated immune cells; enhanced brain uptake of tyrosine and tryptophan (precursors for important brain neurotransmitters); reduced output of free fatty acids from adipose stores; accelerated potassium uptake by cells; and increased metabolic rate. Additionally, insulin mediates the thermogenic effects of carbohydrates, which typically cause increases in metabolic rate following absorption of dietary carbohydrates. Such mediation occurs through the activation by the insulin of fat burning in "brown fat." Insulin is also required for proper thyroid function, and stimulates activity of the "sodium pump," an enzyme that regulates ion movements and accounts for a significant fraction of the metabolic energy burned everyday. Studies have indicated a tendency for mature adults to lose sensitivity to insulin. A sedentary lifestyle, obesity, and a diet low in fiber and chromium and high in sugars, all contribute to decreased insulin sensitivity. Studies have also found that individuals with impaired insulin sensitivity are at risk for high blood pressure, heart disease, and diabetes.

Numerous scientific studies have found that vanadium and chromium, when ingested, have properties that closely mimic, as well as enhance, many of the physiological effects of insulin. In this respect, it has been found that these elements serve to both increase the effectiveness and enhance the anabolic effects of insulin. Supplementation of these elements into a normal diet has been shown to increase lean body mass without increasing body fat, stabilize blood sugar, i.e., glucose levels, increase the responsiveness of cells to insulin, and lower blood fat levels. By their ability to potentiate the effect of insulin, both vanadium and chromium have been found to enhance the entry of glucose (for energy) and amino acids (for protein synthesis) into muscle cells and inhibit the action of enzymes that catabolize the amino acids and proteins. It has further been found that these particular elements include cholesterol lowering, energy producing, and anabolic promoting properties, while providing an optimal environment for anabolic development, weight/fat loss, and energy output.

Though a large number of dietary supplements are currently known and marketed, no such supplements include a novel mixture of vanadium and chromium so as to enhance and mimic the positive effects that insulin has on the body's metabolism. The present invention overcomes these and other deficiencies associated with the prior art.

BRIEF SUMMARY OF THE INVENTION

It is an object of the present invention to provide a nutritional supplement comprising effective amounts of niacin, chromium, and vanadium, and optionally other vitamins and minerals for enhancing insulin utilization and improving carbohydrate management in mammals.

It is also an object of the invention to provide effective amounts of thiamin, riboflavin, magnesium, and zinc.

It is another object of the invention to provide anabolic vitamins and minerals for use in a nutritional supplement, weight loss, formula, and cholesterol lowering agent.

It is still another object of the invention to provide a nutritional supplement for increasing lean body mass without increasing body fat, stabilizing blood sugar, i.e., glucose levels, and increasing the responsiveness of cells to insulin and lower blood fat levels.

It is yet another object of the invention to provide a method for enhancing the physiological effects of insulin in the body through the judicious administration of selected vitamins and minerals.

These and other objects can be addressed by providing a nutritional supplement comprising:

(a) about $1-3000\times10^{-3}$ parts by weight of niacin;

(b) about $1-2000\times10^{-6}$ parts by weight of chromium; and (c) about $1-25\times10^{-3}$ parts by weight of vanadium.

Further, the nutritional supplement preferably further comprises about $15-3000\times10^{-3}$ parts by weight of thiamin, about $1-1000\times10^{-3}$ parts by weight of riboflavin, about $25-2500\times10^{-3}$ parts by weight of magnesium, and/or about $1-100\times10^{-3}$ parts by weight of zinc. The minerals can be provided as inorganic or organic salts, but preferably are provided in bioavailable form as amino acid chelates.

A method for enhancing the physiological effects of insulin comprises administering an effective amount of a nutritional supplement comprising:

(a) about $1-3000\times10^{-3}$ parts by weight of niacin;

(b) about $1-2000\times10^{-6}$ parts by weight of chromium; and (c) about $1-25\times10^{-3}$ parts by weight of vanadium.

DETAILED DESCRIPTION

Before the present composition and method for improved carbohydrate management in mammals are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

The publications and other reference materials referred to herein to describe the background of the invention and to provide additional detail regarding its practice are hereby incorporated by reference. The references discussed herein are provided solely for their disclosure prior to the filing date of the present application. Nothing herein is to be construed as an admission that the inventors are not entitled to antedate such disclosure by virtue of prior invention.

It must be noted that, as used in this specification and the appended claims, the singular forms "a," "an," and "the" include plural referents unless the context clearly dictates otherwise. Thus, for example, reference to a composition containing "an amino acid chelate" includes a mixture of two or more of such amino acid chelates, reference to "a pharmaceutical necessity" includes reference to one or more of such pharmaceutical necessities, and reference to "a diluent" includes reference to a mixture of two or more of such diluents.

In describing and claiming the present invention, the following terminology will be used in accordance with the definitions set out herein.

As used herein, "comprising," "including," "containing," "characterized by," and grammatical equivalents thereof are inclusive or open-ended terms that do not exclude additional, unrecited elements or method steps. "Comprising" is to be interpreted as including the more restrictive terms "consisting of" and "consisting essentially of."

As used herein, "consisting of" and grammatical equivalents thereof exclude any element, step, or ingredient not specified in the claim.

As used herein, "consisting essentially of" and grammatical equivalents thereof limit the scope of a claim to the specified materials or steps and those that do not materially affect the basic and novel characteristic or characteristics of the claimed invention.

As used herein, "tablets" are solid pharmaceutical dosage forms containing nutrient substances with or without suitable diluents and prepared either by compression or molding methods well known in the art. Tablets have been in widespread use since the latter part of the 19$^{th}$ century and their popularity continues. Tablets remain popular as a dosage form because of the advantages afforded both to the manufacturer (e.g., simplicity and economy of preparation, stability, and convenience in packaging, shipping, and dispensing) and the patient (e.g., accuracy of dosage, compactness, portability, blandness of taste, and ease of administration). Although tablets are most frequently discoid in shape, they may also be round, oval, oblong, cylindrical, or triangular. They may differ greatly in size and weight depending on the amount of nutrient substance present-and the intended method of administration. They are divided into two general classes, (1) compressed tablets, and (2) molded tablets or tablet triturates. In addition to the active ingredient or ingredients, tablets contain a number or inert materials or additives. A first group of such additives includes those materials that help to impart satisfactory compression characteristics to the formulation, including diluents, binders, and lubricants. A second group of such additives helps to give additional desirable physical characteristics to the finished tablet, such as disintegrators, colors, flavors, and sweetening agents.

As used herein, "diluents" are inert substances added to increase the bulk of the formulation to make the tablet a practical size for compression. Commonly used diluents include calcium phosphate, calcium sulfate, lactose, kaolin, mannitol, sodium chloride, dry starch, powdered sugar, silica, and the like.

As used herein, "binders" are agents used to impart cohesive qualities to the powdered material. Binders, or "granulators" as they are sometimes known, impart a cohesiveness to the tablet formulation, which insures the tablet remaining intact after compression, as well as improving the free-flowing qualities by the formulation of granules of desired hardness and size. Materials commonly used as binders include starch; gelatin; sugars, such as sucrose, glucose, dextrose, molasses, and lactose; natural and synthetic gums, such as acacia, sodium alginate, extract of Irish moss, panwar gum, ghatti gum, mucilage of isapol husks, carboxymethylcellulose, methylcellulose, polyvinylpyrrolidone, Veegum, microcrystalline cellulose, microcrystalline dextrose, amylose, and larch arabogalactan, and the like.

As used herein, "lubricants" are materials that perform a number of functions in tablet manufacture, such as improving the rate of flow of the tablet granulation, preventing adhesion of the tablet material to the surface of the dies and punches, reducing interparticle friction, and facilitating the ejection of the tablets from the die cavity. Commonly used lubricants include talc, magnesium stearate, calcium stearate, stearic acid, and hydrogenated vegetable oils. Preferred amounts of lubricants range from about 0.1% by weight to about 5% by weight.

As used herein, "disintegrators" or "disintegrants" are substances that facilitate the breakup or disintegration of tablets after administration. Materials serving as disintegrants have been chemically classified as starches, clays, celluloses, algins, or gums. Other disintegrators include Veegum HV, methylcellulose, agar, bentonite, cellulose and wood products, natural sponge, cation-exchange resins, alginic acid, guar gum, citrus pulp, cross-linked polyvinylpyrrolidone, carboxymethylcellulose, and the like.

As used herein, "coloring agents" are.agents that give tablets a more pleasing appearance, and in addition help the manufacturer to control the product during its preparation and help the user to identify the product. Any of the approved certified water-soluble FD&C dyes, mixtures thereof, or their corresponding lakes may be used to color tablets. A color lake is the combination by adsorption of a water-soluble dye to a hydrous oxide of a heavy metal, resulting in an insoluble form of the dye.

As used herein, "flavoring agents" vary considerably in their chemical structure, ranging from simple esters, alcohols, and aldehydes to carbohydrates and complex volatile oils. Synthetic flavors of almost any desired type are now available.

As used herein, "microcrystalline cellulose" means purified, partially depolymerized cellulose prepared by treating a-cellulose, obtained as a pulp from fibrous plant material, with mineral acids. E.g., U.S. Pat. No. 3,141,875. Microcrystalline cellulose is used as a tablet diluent and disintegrant. It is compressed into self-binding tablets that disintegrate rapidly when placed in water.

As used herein, "stearic acid" means a mixture of stearic acid ($C_{16}H_{36}O_2$=284.48) and at palmitic acid ($C_{16}H_{32}O_2$=256.43), which together constitute not less than 90% of the total content, wherein the content of $C_{16}H_{36}O_2$ is not less than 40% of the total. Stearic acid is used as an enteric tablet coating and formulation aid.

As used herein, "magnesium stearate" means a compound of magnesium with a mixture of solid organic acids obtained from fats, and chiefly consists of variable proportions of magnesium stearate and magnesium palmitate. It is used as a pharmaceutical necessity (lubricant) in the manufacture of compressed tablets.

As used herein, "pharmaceutical necessities" means substances that are of little or no therapeutic value, but which are useful in the manufacture and compounding of various pharmaceutical preparations. These substances include antioxidants and preservatives; coloring, flavoring, and diluting agents; emulsifying and suspending agents; ointment bases;

pharmaceutical solvents; and miscellaneous agents. See Remington's Pharmaceutical Sciences.

As used herein, "effective amount" means an amount of a vitamin or mineral that is nontoxic but sufficient to provide the desired local or systemic effect and performance at a reasonable benefit/risk ratio attending any medical treatment. For example, an effective amount of a lubricant is an amount sufficient to function for lubricating the composition for tableting purposes without providing any detrimental effects.

In accordance with a preferred embodiment of the present invention, there is provided a composition for use as a nutritional supplement. The formulation preferably includes niacin, chromium, and vanadium, and optionally other vitamins and minerals in optimal ratios to assure optimal delivery of the vitamins and minerals to various tissues and organs, which are essential for sustaining an anabolic physiological state and for managing carbohydrates in humans and other mammals.

In its most fundamental form, the nutritional supplement composition of the present invention includes a blend of niacin, chromium, and vanadium in the following ranges:

| Basic Ingredients | Ranges in Parts by Weight | |
|---|---|---|
| | Preferred | More Preferred |
| Niacin | $1-3000 \times 10^{-3}$ | $1-250 \times 10^{-3}$ |
| Chromium | $1-2000 \times 10^{-6}$ | $1-1000 \times 10^{-6}$ |
| Vanadium | $1-25 \times 10^{-3}$ | $1-20 \times 10^{-3}$ |

Niacin (nicotinic acid) and niacinarnide (nicotinamide) have identical properties as vitamins. Therefore, as used herein, "niacin" includes niacinamide. In the body niacin is converted to niacinamide, which is an essential constituent of coenzymes I and II that occur in a wide variety of enzyme systems involved in anaerobic oxidation of carbohydrates. The coenzyme serves as a hydrogen acceptor in the oxidation of the substrate. These enzymes are present in all living cells and take part in many reactions of biological oxidation. Nicotinamide-adenine dinucleotide (NAD) and nicotinamide-adenine dinucleotide phosphate (NADP) are coenzymes synthesized in the body that take part in the metabolism of all living cells. Since they are of such widespread and vital importance, it is not difficult to see why serious disturbance of metabolic processes occurs when the supply of niacin to the cell is interrupted. Niacin is readily absorbed from the intestinal tract, and large doses may be given orally or parenterally with equal effect. Further, niacin improves circulation and reduces the cholesterol level in the blood; maintains the nervous system; helps metabolize protein, sugar & fat; reduces high blood pressure; increases energy through proper utilization of food; prevents pellagra; and helps maintain a healthy skin, tongue, and digestive system.

Further, niacin improves the efficiency of chromium and carbohydrate utilization. Niacin is often recommended as the first drug of choice when dietary intervention fails to adequately reduce elevated LDL cholesterol levels. Niacin is also effective in decreasing triglycerides in total cholesterol. Additionally, the vasodilating properties of niacin have been used to enhance blood flow in a variety of vascular disturbances, including conditions where vasospasms are considered to be part of the problem. Thus, as used in the present formula, niacin is important for its ability to cause blood vessels to dilate and its ability to reduce cholesterol levels.

Chromium is an important trace element wherein the lack of sufficient chromium in the diet leads to impairment of glucose utilization, however, disturbances in protein and lipid metabolism have also been observed. Impaired glucose utilization occurs in many middle-aged and elderly human beings. In experimental studies, significant numbers of such persons have shown improvement in their glucose utilization after treatment with chromium. Chromium is transported by transferrin in the plasma and competes with iron for binding sites. Chromium as a dietary supplement may produce benefits due to its enhancement of glucose utilization and its possible facilitating the binding of insulin to insulin receptors, which increases its effects on carbohydrate and lipid metabolism. Chromium as a supplement may produce benefits in atherosclerosis, diabetes, rheumatism, and weight control.

Chromium possesses properties that both mimic and enhance the effects of insulin. When enhancing the effects of insulin, chromium indirectly assists amino acid uptake by muscle, stimulates protein synthesis, and retards the rate of protein breakdown. Additionally, by normalizing blood sugar, biologically active chromium may break the cycle of alternating hyper- and hypo-glycemia, with its consequence of overeating and weight gain. There have been many anecdotal reports that chromium can curb sugar cravings. Additionally, by promoting insulin-stimulated brain uptake of tryptophan, it has also been found that chromium may aid brain synthesis of serotonin, a neurotransmitter than helps control appetite and especially sugar cravings. Additionally, since insulin stimulates protein synthesis and retards protein breakdown in skeletal muscle and other tissues, the chromium potentiation of this effect could be especially valuable to dieters by burning fat and to athletes for the development of muscle.

Previous clinical studies with supplemental chromium have shown modest improvements in glucose tolerance. A prime reason for the realization of only modest improvements is attributed to the relatively poor absorption of nutritional (trivalent) chromium. In this respect, trivalent chromium has a strongly positive charge that impedes its movement across cell membranes. Due to the presence of competing ions such as copper, iron, manganese, and zinc in the human body, adequate absorption of chromium occurs best when the metal is provided in chelated form, such as amino acid chelates, vitamin acid chelates, and the like. An especially preferred form of chromium according to the present invention is as chromium nicotinate glycinate.

Vanadium is an essential nutrient beneficial for thyroid hormone metabolism. The daily requirement necessary to prevent a deficiency is about 10 to 20 micrograms per day. Vanadium deficiency can lead to slow growth, defective bones, and altered lipid metabolism. Vanadium exerts an insulin-like effect in some respects, and there has been a considerable amount of research on vanadium and diabetes. In insulin dependent diabetics, vanadium has been found to reduce the amount of insulin required to manage the disease, and in non-insulin dependent diabetics, vanadium has been known to control the condition altogether. Research has shown that supplementation with vanadium leads to an increase in glucose transport into cells, which suggests that vanadium supplementation of the diet improves glucose metabolism and may aid in preventing diabetes.

Once ingested, vanadium typically is transformed into vanadate, the salt form of vanadic acid. It has been found that vanadate ions will mimic all or most of the action of insulin in intact cell systems via a post-receptor mechanism. In various tissues certain metabolic effects of insulin require phosphorylation reactions. Phosphorylation generally means a metabolic process of introducing a phosphate group into an organic molecule. For example, when insulin binds the fat cells, it causes phosphorylation of the amino acids, threonine, tyrosine, and serine in the insulin receptors of the fat cells and thus stimulates glucose transport, glycogen synthesis, and glucose oxidation. It has been found that vanadate, like insulin, also causes phosphorylation of the insulin receptors of fat cells and thus stimulates glucose transport, activates glycogen synthase, and increases glycogen synthesis in the fat cells. Indeed, experimental studies have concluded that vanadate and insulin cause qualitatively similar changes in muscle glucose metabolism. These studies have also indicated that the ability of vanadate to mimic insulin action may be attributed to either the anion's ability to participate in reduction-oxidation processes, or to regulate (inhibit) phosphotransferase activity.

It has been found that vanadate stimulates carbohydrate uptake in the liver. In contrast, insulin does not stimulate glucose transport in this tissue, although insulin binding and stimulation of diverse biochemical processes have been previously demonstrated. Additionally it has also been found that vanadate does not increase serum insulin levels, which therefore suggests that insulin target tissues themselves are not the site of vanadate action.

As previously indicated, vanadate is operable to activate glycogen synthase. Glycogen synthase is an enzyme that causes the conversion of glucose into glycogen. Glycogen itself is a polysaccharide that is the chief carbohydrate storage material in humans. It has been found that maximum glycogen synthase activation produced by vanadate is indistinguishable from that of insulin. Evidence that strongly suggests a common mechanism of action for insulin and vanadate includes the following findings: with maximum insulin, additional quantities of vanadate are without effect; with submaximal insulin, additional quantities of vanadate increase both the glycogen synthase activation state and 2-deoxyglucose transport to the level obtained with maximum insulin; insulin and vanadate counteract the activating effect of adrenalin on glycogen phosphorylase in a similar manner, adrenalin partially reverses vandate and insulin activated glycogen synthase in a similar manner; and vanadate and insulin activate glycogen synthase within similar time frames. Thus, the presence of in vivo vanadate from the ingestion of vanadium can lead to stable, long lasting, normoglycemic and anabolic states and restore tissue responsiveness to insulin without apparent signs of toxicity.

It is also preferable that the formulation contain one or more additional ingredients selected from the group consisting of vitamins and minerals that enhance the utilization of carbohydrates. Preferred formulations and ranges of these ingredients are:

| Additional Ingredients | Ranges in Parts by Weight | |
|---|---|---|
| | Preferred | More Preferred |
| Thiamin | $15–3000 \times 10^{-3}$ | $15–100 \times 10^{-3}$ |
| Riboflavin | $1–1000 \times 10^{-3}$ | $1–500 \times 10^{-3}$ |
| Magnesium | $25–2500 \times 10^{-3}$ | $25–250 \times 10^{-3}$ |
| Zinc | $1–100 \times 10^{-3}$ | $1–50 \times 10^{-3}$ |

Riboflavin is another B vitamin, which plays its physiological role as the prosthetic group of a number of enzyme systems that are involved in the oxidation of carbohydrates and amino acids. It functions in combination with a specific protein either as a mononucleotide containing phosphoric acid (FMN), or as a dinucleotide combined through phosphoric acid with adenine (FAD). The specificity of each of the enzymes is determined by the protein in the complex. By a process of oxidation-reduction, riboflavin in the system either gains or loses hydrogen. The substrate, either carbohydrate or amino acid, may be oxidized by a removal of hydrogen. The first hydrogen acceptor in the chain of events is NAD or NADP, the di- or tri-nucleotide containing nicotinic acid and adenine. The oxidized riboflavin system then serves as hydrogen acceptor for the coenzyme system and in turn is oxidized by the cytochrome system. The hydrogen is finally passed on to the oxygen to complete the oxidative cycle. A number of flavoprotein enzymes have been identified, each of which is specific for a given substrate. Riboflavin also aids in the formation of antibodies and red blood cells; maintains cell respiration; necessary for the maintenance of good vision, skin, nails and hair; alleviates eye fatigue; and promotes general health.

Thiamin or thiamine is a generic term applied to all substances possessing vitamin B-1 activity, regardless of the anion attached to the molecule. The cationic portion of the molecule is made up of a substituted pyrimidine ring connected by a methylene bridge to the nitrogen of a substituted thiazole ring. In a phosphorylated form, thiamine serves as the prosthetic group of enzyme systems that are concerned with the decarboxylation of $\alpha$-ketoacids. Some decarboxylation reactions are reversible, so that synthesis (condensation) may be achieved. Thus, thiamine is also important to the biosynthesis of keto-acids. It is involved in transketolase reactions. Thiamine is readily absorbed in aqueous solution from both the small and large intestine, and is then carried to the liver by the portal circulation. In the liver, as well as in all living cells, it normally combines with phosphate to form cocarboxylase. It may be stored in the liver in this form or it may combine further with manganese and specific proteins to become active enzymes known as carboxylases. Thiamine also plays a key role in the body's metabolic cycle for generating energy; aids in the digestion of carbohydrates; is essential for the normal functioning of the nervous system, muscles & heart; stabilizes the appetite; and promotes growth & good muscle tone.

Magnesium is the second most plentiful cation of the intracellular fluids. It is essential for the activity of many enzyme systems and plays an important role with regard to neurochemical transmission and muscular excitability. Deficits are accompanied by a variety of structural and functional disturbances. The average 70-kg adult has about 2000 mEq of magnesium in his body. About 50% of this magnesium is found in bone, 45% exists as an intracellular cation, and 5% is in the extracellular fluid. About 30% of the magnesium in the skeleton represents an exchangeable pool present either within the hydration shell or on the crystal surface. Mobilization of the cation from this pool in bone is fairly rapid in children, but not in adults. The larger fraction of magnesium in bone is apparently an integral part of bone crystal.

The average adult in the United States ingests about 20 to 40 mEq of magnesium per day in an ordinary diet, and of this about one third is absorbed from the gastrointestinal tract. The evidence suggests that the bulk of the absorption occurs in the upper small bowel. Absorption is by means of an active process apparently closely related to the transport system for calcium. Ingestion of low amounts of magnesium results in increased absorption of calcium and vice versa.

Magnesium is a cofactor of all enzymes involved in phosphate transfer reactions that utilize adenosine triphosphate (ATP) and other nucleotide triphosphates as substrates. Various phosphatases and pyrophosphatases also represent enzymes from an enormous list that are influenced by this metallic ion.

Magnesium plays a vital role in the reversible association of intracellular particles and in the binding of macromolecules to subcellular organelles. For example, the binding of messenger RNA (mRNA) to ribosomes is magnesium dependent, as is the functional integrity of ribosomal subunits. Certain of the effects of magnesium on the nervous system are similar to those of calcium. An increased concentration of magnesium in the extracellular fluid causes depression of the central nervous system (CNS). Hypomagnesemia causes increased CNS irritability, disorientation, and convulsions. Magnesium also has a direct depressant effect on skeletal muscle. Abnormally low concentrations of magnesium in the extracellular fluid result in increased acetylcholine release and increased muscle excitability that can produce tetany.

Zinc is known to occur in many important metalloenzymes. These include carbonic anhydrase, carboxypeptidases A and B, alcohol dehydrogenase, glutamic dehydrogenase, D-glyceraldehyde-3-phosphate dehydrogenase, lactic dehydrogenase, malic dehydrogenase, alkaline phosphatase, and aldolase. Impaired synthesis of nucleic acids and proteins has been observed in zinc deficiency. There is also evidence that zinc may be involved in the secretion of insulin and in the function of the hormone.

The mineral ingredients in the present invention can be supplied as inorganic salts, such as chlorides, sulfates, nitrates, and the like; organic salts, such as citrates, tartrates, bitartrates, lactates, phosphates, malates, maleates, fumarates, succinates, acetates, palmeates, stearates, oleates, palmitates, laurates, valerates, taurinates, and the like, or in bioavailable form, such as amino acid chelates. For example, preferred forms of the chromium, vanadium, magnesium, and zinc minerals are chromium nicotinate glycinate, vanadyl sulfate, magnesium taurinate, and zinc taurinate, respectively.

Bioavailable forms of magnesium, zinc, and chromium, which are utilized in facilitating anabolism, are made by chelating or complexing the mineral with an amino acid or peptide ligand. The ligand to mineral ratio in these chelates is at least 1:1 and is preferably 2:1 or higher. The molecular weight of these amino acid chelates is not greater than 1,500 daltons and preferably does not exceed 1,000 daltons. Such amino acid chelates are stable and are generally taught in the prior art to be absorbed intact through the intestinal tract via an active dipeptide transport system. It has not previously been known that, when properly administered, such chelates can cooperate with properly blended vitamins to improve management of carbohydrates and affect sustained anabolism. Such amino acid chelates have a stability constant of between about $10^6$ and $10^{16}$. A more detailed description of such chelates and the method by which they are absorbed through the intestine is documented in U.S. Pat. No. 4,863,898 and also in H.D. Ashmead et al., Intestinal Absorption of Metal Ions and Chelates, (Charles C. Thomas, Springfield, Ill., 1985).

To clarify what is meant by the term "amino acid chelate" the American Association of Feed Control Officials has issued the following official definition: "amino acid chelate-a metal ion from a soluble salt with amino acids with a mole ratio of one mole of metal to one to three (preferably two) moles of amino acids to form coordinate covalent bonds. The average weight of the hydrolyzed amino acids must be approximately 150 and the resulting molecular weight of the chelate must not exceed 800." It is also now well documented that amino acid chelates can be prepared from metal ions that do not come from soluble salts. U.S. Pat. No. 4,599,152 and U.S. Pat. No. 4,830,716 both disclose methods of preparing pure or pharmaceutical grade amino acid chelates using metal sources other than soluble metal salts. While, the manner these amino acid chelates are made is not essential to the present invention, provided they meet the criteria stated above, it is preferable that pharmaceutical grade chelates be used to minimize the presence of unwanted impurities such as sulfate ions, excess chloride ions, and the like.

As referenced above, various studies have found that minerals in the form of amino acid chelates, composed of amino acid ligands or combinations of amino acid and vitamin acid ligands, (e.g., glycinates, arginates, and nicotinate glycinates), render the minerals more readily absorbable. The reason for this is the transport of amino acid chelates across the intestinal mucosa and into the portal circulation is accomplished by an amino acid transport mechanism and not by traditional mineral ion transport. Once in the blood, the amino acid chelates do not bind directly to serum proteins, including albumin, ceruloplasmin, transferrin, and the like, but are transported directly to target tissues in the chelated form. Thereafter, the mineral is released from the chelate intracellularly. Importantly, this indirect transport results in greatly improved bioavailability of the minerals to organs and cells and works independently of either mineral-saturated or reduced concentrations of serum proteins. Additionally, unlike most conventional mineral salts that are commercially available, amino acid chelates do not cause changes in bowel habits after oral administration. This is in contrast to notable examples of conventional magnesium salts such as magnesium citrate, which commonly causes loose stools or diarrhea.

While the amino acid or peptide ligands used in formulating the amino acid chelates are in themselves important nutrients, they may or may not be present in sufficient amounts to materially contribute as protein calorie sources in the present invention. In any event, they are important factors in furthering the cause of anabolism.

The composition of the present invention can be formulated in any conventional dosage form, such as tablets, capsules, powders, liquids, and the like. Preferably, the composition is formulated as a tablet, and as such can include formulation aids or pharmaceutical necessities according to methods and procedures well known in the art. In general, the ingredients are mixed together and then formed into tablets under pressure in a press.

The preferred daily dosage of the composition ranges from about 1–20 mg of active ingredients per kg of body weight. For use as a basic nutritional supplement, it is recommended that a 70-kg person take about three tablets containing about 140 mg of active ingredients with high carbohydrate meals per day. As a dietary supplement for athletes, it is recommended that two 140-mg tablets be taken with a high complex carbohydrate snack about half an hour before activity or a workout. On non-active days the composition can be taken as a basic nutritional supplement.

EXAMPLE

The following formulae represent specific embodiments of the invention. These embodiments can be prepared in the manner indicated above by blending together the stated raw materials in an agglomerator so as to result in product having a uniform composition with the precise proportions of the components as indicated. The agglomerated material is then pressed into tablets, encapsulated, packaged in a suitable container, or dissolved in liquid to achieve the finished product. In the preferred embodiment, the composition comprises the following ingredients stated in amounts by weight:

|  | Formulation Number | | | | | | |
|---|---|---|---|---|---|---|---|
| Ingredients | I | II | III | IV | V | VI | VII |
| Niacin (mg) | 125 | 25 | 25 | 100 | 50 | 150 | 10 |
| Chromium (μg) | 1000 | 200[a] | 1000 | 100 | 100 | 200 | 400 |
| Vanadium (mg) | 16 | 5 | 16 | 1 | 10 | 20 | 20 |
| Thiamin (mg) | — | 25 | 100 | — | — | — | 10 |
| Riboflavin (mg) | — | 10 | — | 50 | — | — | 10 |
| Magnesium (mg) | — | 70[b] | — | — | 82 | — | 50 |
| Zinc (mg) | — | 5[c] | — | — | — | 5 | 10 |

[a]chromium nicotinate glycinate
[b]magnesium taurinate
[c]zinc taurinate

What is claimed is:

1. A method for enhancing the physiological effects of insulin comprising administering an effective amount of a nutritional supplement consisting essentially of:

(a) $25 \times 10^{-3}$ parts by weight of niacin;

(b) $200 \times 10^{-6}$ parts by weight of chromium nicotinate glycinate;

(c) $5 \times 10^{-3}$ parts by weight of vanadyl sulfate;

(d) $25 \times 10^{-3}$ parts by weight of thiamin;

(e) $10 \times 10^{-3}$ parts by weight of riboflavin;

(f) $70 \times 10^{-3}$ parts by weight of magnesium taurinate;

(g) $5 \times 10^{-3}$ parts by weight of zinc taurinate;

(h) effective amounts of microcrystalline cellulose, stearic acid, and magnesium stearate as formulation aids.

* * * * *